(12) United States Patent
Tanii et al.

(10) Patent No.: US 9,138,146 B2
(45) Date of Patent: Sep. 22, 2015

(54) BIOLOGICAL OPTICAL MEASUREMENT INSTRUMENT AND REFERENCE IMAGE DISPLAY METHOD

(75) Inventors: Michiyo Tanii, Tokyo (JP); Shingo Kawasaki, Tokyo (JP); Michiyuki Fujiwara, Tokyo (JP); Joerg Schnackenberg, Tokyo (JP); Akihiko Toda, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 742 days.

(21) Appl. No.: 13/501,815

(22) PCT Filed: Oct. 8, 2010

(86) PCT No.: PCT/JP2010/067728
§ 371 (c)(1),
(2), (4) Date: Apr. 13, 2012

(87) PCT Pub. No.: WO2011/046072
PCT Pub. Date: Apr. 21, 2011

(65) Prior Publication Data
US 2012/0203088 A1    Aug. 9, 2012

(30) Foreign Application Priority Data
Oct. 14, 2009   (JP) ................................. 2009-237224

(51) Int. Cl.
*A61B 6/00* (2006.01)
*A61B 5/00* (2006.01)
*A61B 5/02* (2006.01)
*A61B 5/145* (2006.01)

(52) U.S. Cl.
CPC ........... *A61B 5/0059* (2013.01); *A61B 5/02028* (2013.01); *A61B 5/14546* (2013.01); *A61B 5/6814* (2013.01); *A61B 2562/0233* (2013.01); *A61B 2562/046* (2013.01)

(58) Field of Classification Search
USPC .................................................. 600/476–479
See application file for complete search history.

(56) References Cited

U.S. PATENT DOCUMENTS

2006/0100526 A1*   5/2006   Yamamoto et al. ........... 600/476
2006/0184044 A1*   8/2006   Kaga et al. .................... 600/476

FOREIGN PATENT DOCUMENTS

| JP | 2001-79008 A | 3/2001 |
|---|---|---|
| JP | 2001-137217 A | 5/2001 |
| JP | 2003-75331 A | 3/2003 |
| JP | 2003-88528 A | 3/2003 |
| JP | 2006-122086 A | 5/2006 |
| JP | 2007-185491 A | 7/2007 |
| JP | 2009-261588 A | 11/2009 |

OTHER PUBLICATIONS

International Search Report mailed Nov. 30, 2010 in International Application No. PCT/JP2010/067728.

* cited by examiner

*Primary Examiner* — Joel F Brutus
(74) *Attorney, Agent, or Firm* — Brundidge & Stanger, P.C.

(57) ABSTRACT

The biological optical measurement instrument is provided with a mobile position sensor that can move in a 3-dimensional space and that detects spatial position in the 3-dimensional space, a head-surface image creating unit that creates a head-surface image of an object and a head-surface point creating unit that creates, on the head-surface image, a head-surface point corresponding to the spatial position of the mobile position sensor.

11 Claims, 9 Drawing Sheets

BIOLOGICAL OPTICAL MEASUREMENT INSTRUMENT AND REFERENCE IMAGE DISPLAY METHOD

FIELD OF THE INVENTION

The present invention relates to a biological optical measurement instrument which irradiates near-infrared light to a living body and measures the light passed through the body or reflected inside of the body so as to measure in-vivo blood circulation, hemodynamic status and variation of hemoglobin concentration, and the method for displaying reference images.

DESCRIPTION OF RELATED ART

A biological optical measurement instrument is capable of harmlessly measuring blood circulation, hemodynamic status and variation of hemoglobin concentration in an object without putting the object under much restriction by applying on the object the probes in which plural optical fibers (light transmission units) are mounted. As the method for displaying the measured data, variation of hemoglobin is displayed using a graph or grayscale image.

Regarding the time that a probe holder is applied on an object, Patent Document 1 discloses the technique for detecting the position of probe holder by a magnetic sensor to improve repeatability of probe holder application. Patent Document 1 first determines a target region on a reference image of an object, and determines a suggested probe holder position based on the position of the target region. Then the current position of the probe holder is detected, the distance between the suggested position of probe holder and the current position of probe holder is calculated, and when the calculated distance falls within a predetermined range the notification is made by means such as sound alarm.

PRIOR ART DOCUMENTS

Patent Documents

Patent Document 1: JP-A-2006-122086

However, though the position of a probe holder can be figured out by the technique disclosed in Patent Document 1 with respect to an object, the setting position of optical fibers in the probe holder could not be verified in real time. Thus an error could occur at each measurement position between the position at which the measurement is performed by the set optical fibers and the position at which an examiner desires to measure.

The objective of the present invention is to provide the biological optical measurement instrument and the reference image display method capable of verifying the setting position of optical fibers (light transmission units) in the probe holder in real time.

BRIEF SUMMARY OF THE INVENTION

In order to achieve the objective of the present invention, the biological optical measurement instrument in the present invention comprises:

a plurality of light transmission units;

a light source unit configured to irradiate near-infrared light to an object to be examined;

an optical measurement unit configure to measure the intensity of transmitted light at a plurality of measurement points in the object;

a probe holder configured to affix the light transmission unit;

a signal processing unit configured to process and image the measurement data from the optical measurement unit; and a display unit configured to display the processing result of the signal processing unit, further comprising:

a mobile position sensor which is movable in a 3-dimensional space and configured to detect the spatial position in the 3-dimensional space;

a head-surface image creating unit configured to create a head-surface image of the object; and a head-surface point creating unit configured to create, on the head-surface image, a head-surface point corresponding to the spatial position of the mobile position sensor.

When the examiner applies a pen-shaped mobile magnetic sensor (mobile position sensor) referred to as a stylus pen to a light transmission unit setting position (hole) of the probe holder attached to the object, the display unit can display the head-surface point corresponding to the spatial position of the mobile magnetic sensor on a head-surface image. In this manner, the examiner can verify whether the current setting positions of the light transmission units are corresponded to the light transmission unit setting points which have been measured in the past in real time.

The objective of the present invention can also be achieved by the reference image display method including:

a step of irradiating near-infrared light to an object to be examined using a plurality of light transmission units affixed to a probe holder;

a step of measuring the intensity of transmitted light at a plurality of measurement points in the object;

a step of processing and imaging the measurement data of the measurement points; and a step of displaying the processing result, further including:

a step of creating a head-surface image of the object; and a step of creating the head-surface point corresponding to the spatial position of a mobile position sensor of which the spatial position can be detected.

Effect of the Invention

In accordance with the present invention, it is possible to verify the setting position of optical fibers (light transmission units) in the probe holder in real time.

DETAILED DESCRIPTION OF THE INVENTION

The embodiments of the present invention will be described below.

Embodiment 1

Figure 1:
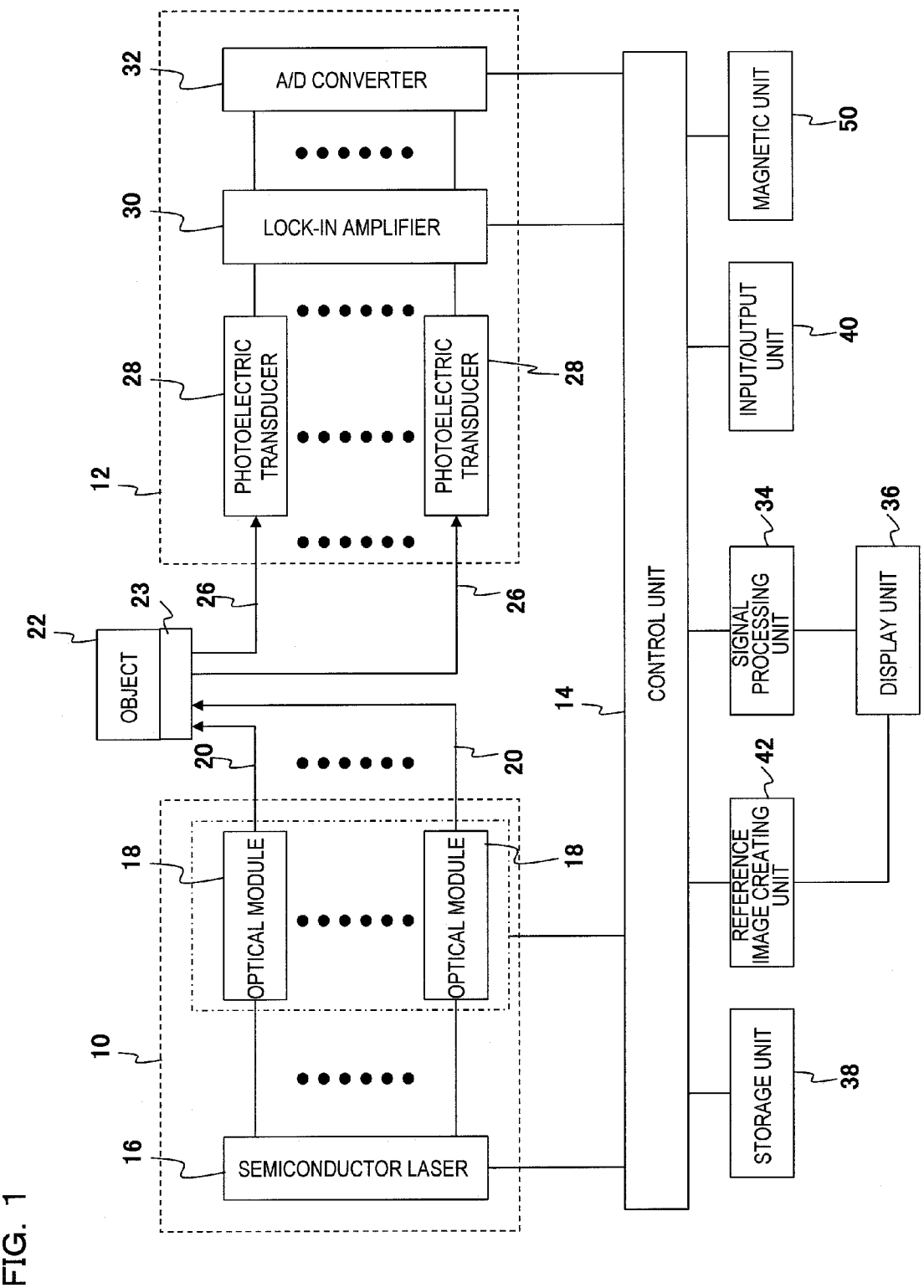
FIG. 1 is a view showing the general configuration of the present invention.

A biological optical measurement instrument irradiates near-infrared light to the inside of an object 22, and detects the light which is reflected from the vicinity of the body surface of the object 22 or transmitted through the object 22 (hereinafter referred to as transmitted light). This biological optical measurement instrument, as shown in FIG. 1, mainly comprises devices such as a light source unit 10 configured to irradiates near-infrared light, a light measurement unit 12 configured to measure the transmitted light and convert it into an electric signal, a control unit 14 configured to control driving of the light source unit 10 and the light measurement unit 12, and a display unit 36.

The light source unit 10 comprises a semiconductor laser configured to eradiate light having a predetermined wavelength, and a plurality of optical modules 18 comprising a modulator for modulating the light generated by the semiconductor laser 16 by a plurality of different frequencies, and the outputted light from the respective optical modules are irradiated to predetermined measurement positions in the object 22 via irradiating optical fibers 20 respectively. A probe holder 23 is attached to the object 22, and the plurality of irradiating optical fibers 20 and detecting optical fibers 26 are detachably applied to the respective setting positions (holes) of the probe holder 23. The irradiating optical fibers 20 can also be referred to as irradiating light transmission units, and the detecting optical fibers 26 can also be referred to as detecting light transmission units. The optical fibers can also be referred to as light transmission units.

The light source unit 10 comprises n-number (n is a positive whole number) of optical modules 18. While the wavelength of light depends on the spectral characteristic of a target subject in the object 22, in the case that the oxygen saturation or amount of blood is measured from the concentration of oxygenated hemoglobin and deoxygenated hemoglobin, one or plural wavelengths are selected and used from the light within the wavelength range of 600 nm~1400 nm. In concrete terms, the light source unit 10 is configured to generate the light having two kinds of wavelengths, for example that are 780 nm and 830 nm, and these two wavelengths of light are synthesized and irradiated from one irradiating position.

The light measurement unit 12 is formed by photoelectric transducers 28 which are photodiode, etc. configured to convert the transmitted light induced from a plurality of measurement positions in the object 22 via detecting optical fibers 26 into the electric quantity corresponding to the light quantity respectively, a lock-in amplifier 30 configured to input the electric signals from the photoelectric transducers 28 and selectively detect the modulated signals corresponding to the light irradiating positions, and an A/D converter 32 configured to convert the output signals from the lock-in amplifier 30 into digital signals. The lock-in amplifier 30 selectively detects the modulated signals corresponding to the light irradiating positions and the two wavelengths.

Also, the biological optical measurement instrument comprises a signal processing unit 34 configured to process the hemoglobin variation signal converted into the digital signal and create a graph for each channel or a 2-dimensional or 3-dimensional grayscale image in which the respective hemoglobin variation signals are interpolated for each channel, a reference image creating unit 42 configured to create a head-surface image, brain-surface image or measurement points, etc. of the object 22, a display unit 36 configured to display the information such as processing result of the signal processing unit 34, a head-surface image, a brain-surface image and measurement points, a storage unit 38 configured to store the necessary data for the process or the processing result of the signal processing unit 34 or the reference image creating unit 42, and an input/output unit 40 configured to input various commands necessary for operating the instrument.

Further, the biological optical measurement instrument comprises a magnetic unit 50 (position sensor unit) configured to verify the optical fiber setting positions of the probe holder 23 for setting the respective optical fibers 20 and 26. The magnetic unit 50 is connected to the control unit 14. The optical fiber setting positions can also be referred to as light transmission unit setting positions.

Figure 2:
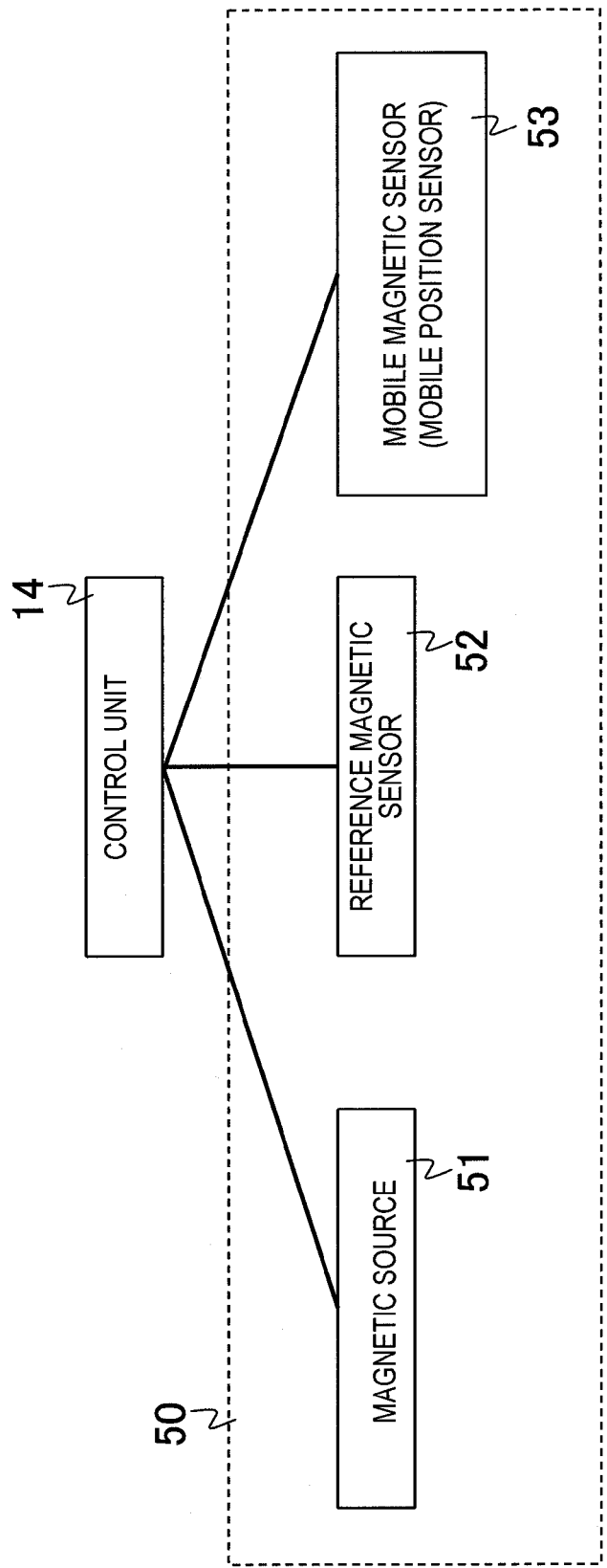
FIG. 2 is a view showing the configuration of a magnetic unit 50 in the present invention.
Figure 3:
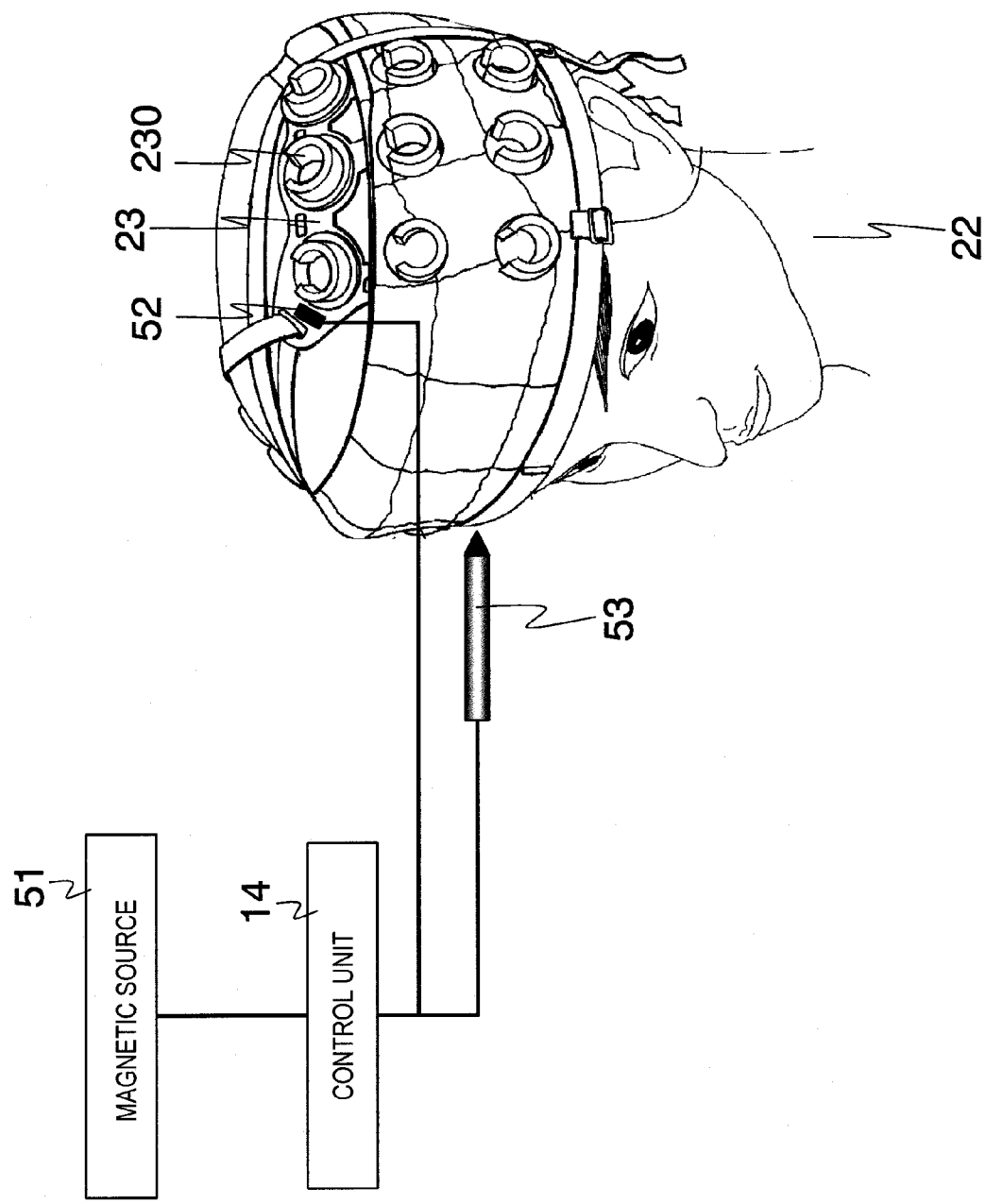
FIG. 3 is a view showing the usage pattern of the magnetic unit 50 in the present invention.

FIG. 2 shows the configuration of the magnetic unit 50 and FIG. 3 shows the usage pattern of the magnetic unit 50. The magnetic unit 50 is formed by a magnetic source 51, a reference magnetic sensor 52 and a mobile magnetic sensor 53 (mobile position sensor). The mobile magnetic sensor 53 is movable in a 3-dimensional space, and is the mobile position sensor which detects the spatial position in the 3-dimensional space. The magnetic source 51, the reference magnetic sensor 52 and the mobile magnetic sensor 53 are respectively connected to the control unit 14. In the probe holder 23, a plurality of holes 230 to be the optical fiber setting positions are provided. In FIG. 3, nine of the holes 230 are provided to the probe holder 23.

The magnetic source 51 is formed by a magnetic field generating coil, and generates the magnetic field of triaxial orthogonal system in a 3-dimensional space. The magnetic source 51 is affixed, for example in the vicinity of a biological optical measurement instrument. The vicinity of the biological optical measurement instrument means the position where the magnetic field from the magnetic source 51 can be received by the reference magnetic sensor 52 and the mobile magnetic sensor 53.

The reference magnetic sensor 52 is the sensor to be placed in the magnetic field space generated by the magnetic source 51, and to be the reference position of the mobile magnetic sensor 53. In concrete terms, as shown in FIG. 3, the reference magnetic sensor 52 is provided to the probe holder 23 which is applied to the object 22.

The mobile magnetic sensor 53 is the mobile position sensor that detects the relative position (spatial position) with respect to the reference position of the reference magnetic sensor 52, capable of causing the display unit 36 to display the special position of the mobile magnetic sensor 53 or storing the spatial position of the mobile magnetic sensor 53 in the storage unit 38 via the control unit 14.

The mobile magnetic sensor 53 is a pen-shaped sensor referred to as a stylus pen, wherein an examiner can hold it in his/her hand and freely move it in the magnetic field space (3-dimensional space) generated by the magnetic source 51. In the mobile magnetic sensor 53, a storage button (not shown in the diagram) is provided for causing the storage unit 34 to store the spatial position of the penpoint. When the storage button of the mobile magnetic sensor 53 is pushed by the examiner, the control unit 14 can cause the storage unit 38 to store the spatial position of the mobile magnetic sensor 53 at the time that the button was pushed.

Figure 4:
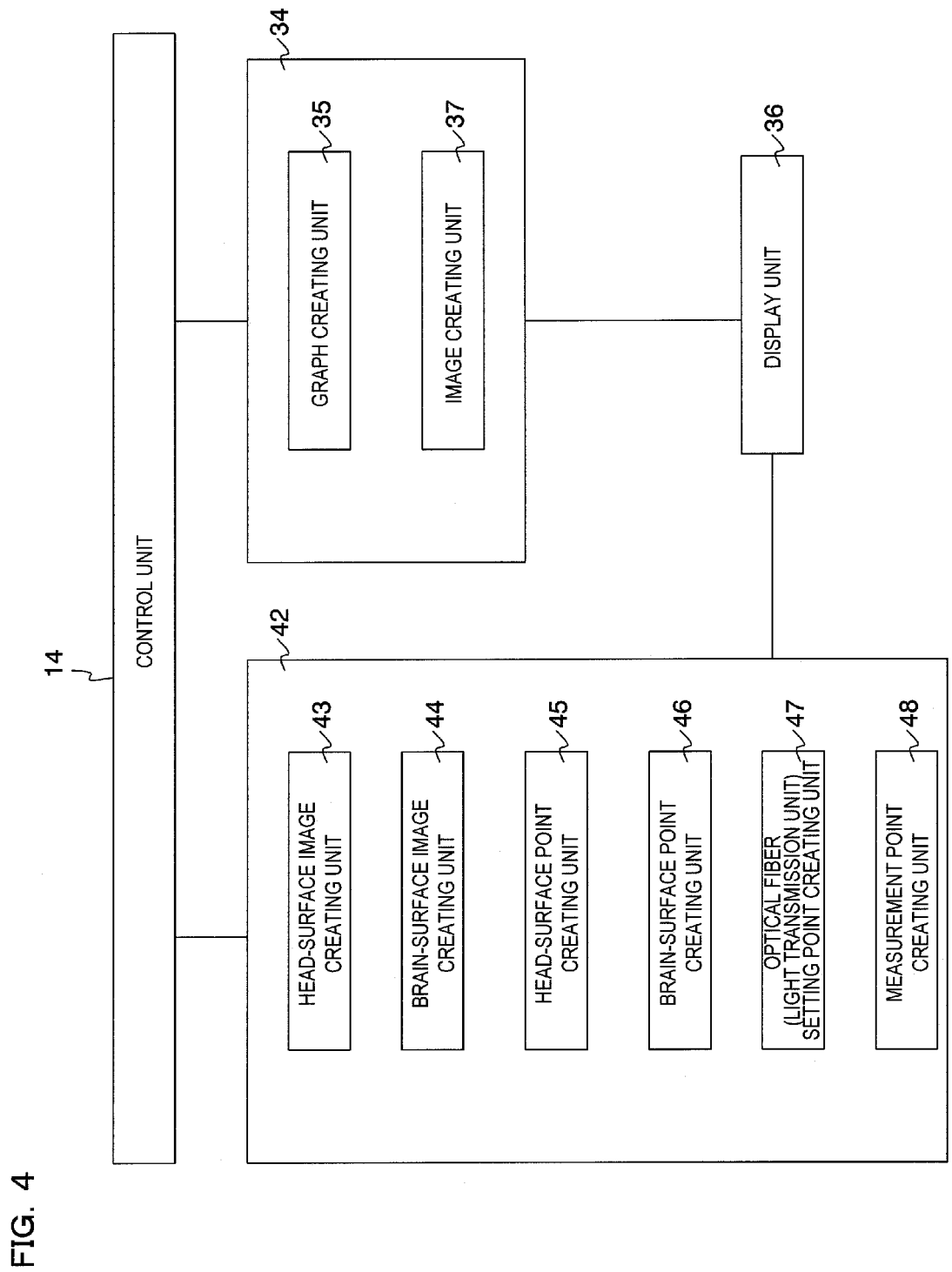
FIG. 4 is a view showing the configuration of a signal processing unit 34 and a reference image creating unit 42 in the present invention.

FIG. 4 shows the configuration of the signal processing unit 34 and the reference image creating unit 42.

The signal processing unit 34 is formed by a graph creating unit 35 configured to process the hemoglobin variation signal converted into the digital signal by the A/D converter 32 and create a graph, for each channel, of concentration change of oxygenated hemoglobin, concentration change of deoxygenated hemoglobin and concentration change of total hemoglobin, etc. and an image creating unit 37 configured to create a grayscale image of the 2-dimensional image or 3-dimensional image in which the hemoglobin variation signal is interpolated for each channel. The channel here is equivalent to a measurement position.

Also, a head-surface image of the 3-dimensional wire frame or 3-dimensional profile image equivalent to the head region of the object 22, a brain-surface image which is the 3-dimensional image of the object 22 obtained using the 3-dimensional image diagnostic apparatus such as an MRI apparatus or an X-ray CT apparatus, and the spatial positions of the optical fiber setting positions (holes) of the probe holder 23 which have been measured in the past are stored in the storage unit 38 in advance.

The reference image creating unit 42 is formed by a head-surface image creating unit 43 configured to read out the head-surface image stored in the storage unit 38 and create a head-surface image corresponding to the size or shape of the head region of the object 22 based on the spatial position in the head surface of the object 22, a brain-surface image creating unit 44 configured to readout the brain-surface image corresponding to the object 22 stored in the storage unit 38 and create a brain-surface image, a head-surface point creating unit 45 configured to create on a head-surface image the spatial position of the head surface of the object 22 corresponding to the point specified by the mobile magnet sensor 53 as a head-surface point, a brain-surface point creating unit 46 configured to create on a brain-surface image the spatial position of the brain surface of the object 22 corresponding to the point specified by the mobile magnetic sensor 53 as a brain-surface point, an optical fiber setting point creating unit 47 configured to read out the spatial position of the optical fiber setting point corresponding to the optical fiber setting position (hole) which has been measured in the past and create the optical fiber setting position on a head-surface image or a brain-surface image, and a measurement point creating unit 48 configured to create on a head-surface image or a brain-surface image the measurement point corresponding to the measurement position equivalent to the center point of the optical fiber setting point. The optical fiber setting point can also be referred to as a light transmission unit setting point.

Here, the pattern for displaying on a head-surface image the optical fiber setting point or a measurement point corresponding to the optical fiber setting point (hole) which has been measured in the past and the head-surface point corresponding to the spatial position of the mobile magnetic sensor 53 will be described.

First, as the initial setting, the head region of the object 22 is measured using the mobile magnetic sensor 53. Regarding the first point, the second point, . . . , to be stored in the mobile magnetic sensor 53, the relative coordinates are measured on the basis of the spatial position of the reference position in the reference magnetic sensor 52, and the spatial positions of the first point, the second point, . . . , are respectively acquired. Then the spatial position of the first point, the second point, . . . , are stored in the storage unit 38.

Figure 5:
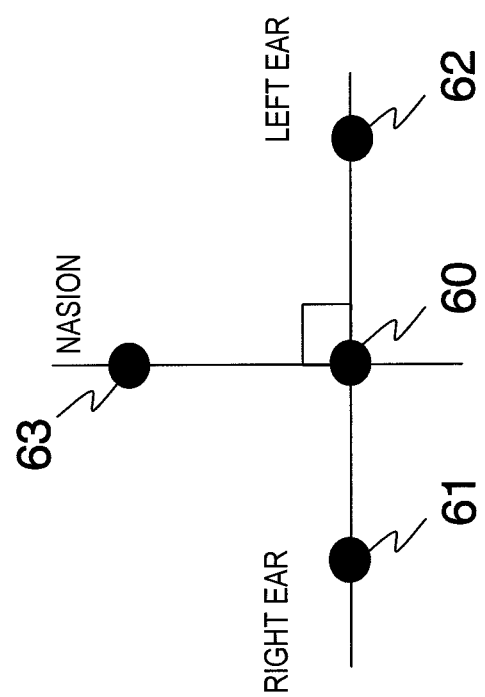
FIG. 5 is a view showing the pattern for calculating a reference point 60 in the present invention.

In concrete terms, as shown in FIG. 5, the first point, the second point and the third point are stored in the storage unit 38 as a nasion (nasal root) 63, a right ear upper-end portion 61 and a left ear upper-end portion 62 defined by the ten-twenty electrode system of the International Federation.

Then the reference image creating unit 42 sets the intersection point at which the straight line drawn between the right ear upper-end portion 61 and the left ear upper-end portion 62 intersects with the vertical line dropped thereto from the nasion 63 as a reference point 60. The reference point 60 is the reference point acquired from the head surface of the object 22. The spatial positions of the measurement points stored on and after the fourth point are calculated respectively with their original point at the reference point 60.

While the reference magnetic sensor 52 is used as the sensor to be the reference position of the mobile magnetic sensor 53 in the present embodiment, the reference magnetic sensor 52 is not necessarily required as long as the spatial position of the mobile magnetic sensor 53 can be acquired accurately with respect to the magnetic source 51. Also, while the case of using the magnetic unit 50 is exemplified, another device such as an optical unit capable of freely moving in a 3-dimensional space and detecting the spatial position of the mobile optical sensor may be used in place of the magnetic unit 50. In other words, the mobile optical sensor is the mobile position sensor which is movable in a 3-dimensional space and detecting the spatial position in the 3-dimensional space.

Figure 6:
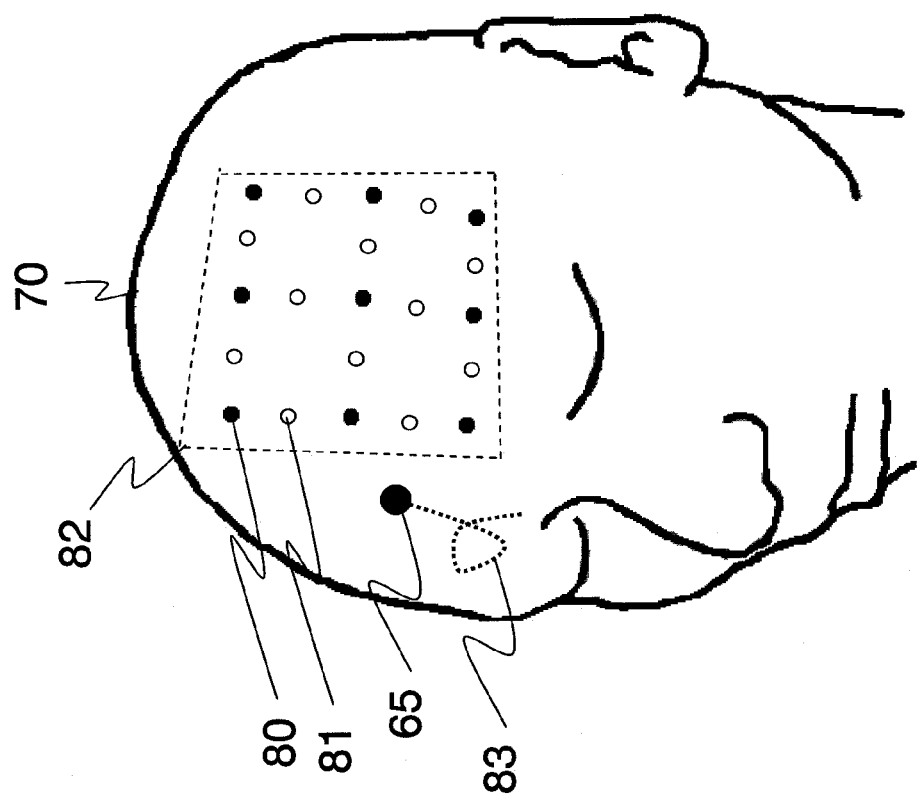
FIG. 6 is a view showing the display pattern of a head-surface image 70 in the present invention.

FIG. 6 shows the display pattern wherein an optical fiber setting point 80 or a measurement point 81 corresponding to the optical fiber setting position (hole) which has been measured in the past and a calculated head-surface point 65 corresponding to the spatial position of the mobile magnetic sensor 53 are displayed on a head-surface image 70.

The head-surface image creating unit 43 first creates the head-surface image 70 by a 3-dimensional wire frame or 3-dimensional pattern image on the basis of the spatial position in which the size or the shape of the head that is the measurement region of the object 22 is measured. In concrete terms, the 3-dimensional wire frame image or the 3-dimensional pattern image corresponding to the size or shape of the head region of the object 22 is created as a head-surface image by executing the parabolic approximation using the spatial positions of the three points (nasion (nasal root) 63, right ear upper-end portion 61 and left ear upper-end portion 62) stored in FIG. 5.

The head-surface point creating unit 45 figures out the spatial position of the whole head-surface image 70 created in the surface image creating unit 43, and corresponds the spatial position of the mobile magnetic sensor 53 to the spatial position of the head-surface image 70. Then the head-surface point creating unit 45 creates on the head-surface image 70 the head-surface point 65 which corresponds to the mobile magnetic sensor 53.

The optical fiber setting point creating unit 47 figures out the spatial position of the whole head-surface image 70 created in the head-surface image creating unit 43, and creates an optical fiber setting point 80 corresponding to the optical fiber setting position (hole) which has been measured in the past on the head-surface image 70. In concrete terms, the optical fiber setting point creating unit 47 reads out from the storage unit 38 the spatial position of the optical fiber setting position (hole) which has been which have been measured in the past. Then the optical setting point creating unit 47 figures out the spatial position of the whole head-surface image 70 created in the head-surface image creating unit 43, and creates the optical fiber setting point 80 which is equivalent to the spatial position of the read out optical fiber setting position (hole).

Also, the measurement point creating unit 48 calculates the spatial position at the midpoint between the optical fiber setting points 80 created by the optical fiber setting point creating unit 47, and creates on the head-surface image 70 the measurement points 81 corresponding to the spatial position of the calculated midpoint, i.e. the measurement position.

Then the display unit 36 displays on the head-surface image 70 the head-surface point 65 and the optical fiber setting point 80 or the measurement point 81 respectively based on the output of the head-surface image creating unit 43, head-surface point creating unit 45, optical fiber setting point creating unit 47 and the measurement point creating unit 48.

The display unit 36 can display on the head-surface image 70, for example the optical fiber setting point 80 or the measurement point 81 which has been measured in the past and the head-surface point 65 corresponding to the mobile magnetic sensor 53. Accordingly, when the examiner applies the pen-shaped mobile magnetic sensor 53, referred to as a stylus pen, to the optical fiber setting position (hole) of the probe holder 23 attached to the object 22, the display unit 36 can display on the head-surface image 70 the optical fiber setting point 80 or the measurement point 81 which has been measured in the past with the head-surface point 65 corresponding to the spatial position of the mobile magnetic sensor 53.

Thus the examiner can verify the setting position (hole) of the currently set optical fiber in real time. The examiner can also verify in real time whether the setting position (hole) of the currently set optical fiber corresponds to the optical fiber setting point 80 or the measurement point 81 which has been measured in the past.

Also, the reference image creating unit 42 can create a holder frame 82 which is equivalent to the circumference of the probe holder 23 from the spatial position of the optical fiber setting point 80 or the measurement point 81 which has been measured in the past, and cause the display unit 36 to display the holder frame 82 on the head-surface image 70. A rectangle-shaped holder frame 82 is formed to cover all of the plural optical fiber setting points 80 which have been measured in the past. The examiner can verify the application position of the whole probe holder 23 from the position of the holder frame 82 with respect to the head-surface image 70.

Further, the head-surface point creating unit 45 can figure out the spatial position of the whole head-surface image 70 created by the head-surface image creating unit 43, and create on the head-surface image 70 a displacement trajectory 83 of the head-surface point 65 corresponding to the spatial position of the mobile magnetic sensor 53. The displacement trajectory 83 of the head-surface point 65 is displayed for a predetermined time (for example, a second) from the timing that the head-surface point 65 moved. The examiner can verify the displacement trajectory of the mobile magnetic sensor 53 from the displacement trajectory of the head-surface point 65.

As described above, in accordance with the first embodiment, the examiner can verify in real time the optical fiber setting position of the probe holder 23 which is for setting the respective optical fibers.

While the present embodiment has been explained using a plurality of irradiating optical fibers (irradiating light transmission units) 20 and detecting optical fibers (detecting light transmission units) 26, the irradiating optical fibers 20 may be replaced with light-emitting diodes (LED) capable of irradiating the light having two wavelengths and the detecting optical fibers 26 may be replaced with photodiodes which detect the light irradiated to the object 22 and outputs the electric signal. At this time, the light source unit 10 executes the operation to emit light by sending the electric signal to the light-emitting diode, and the light measurement unit 12 processes the electric signal from the photodiode and transmits the processed light to the signal processing unit 34.

Embodiment 2

Figure 7:
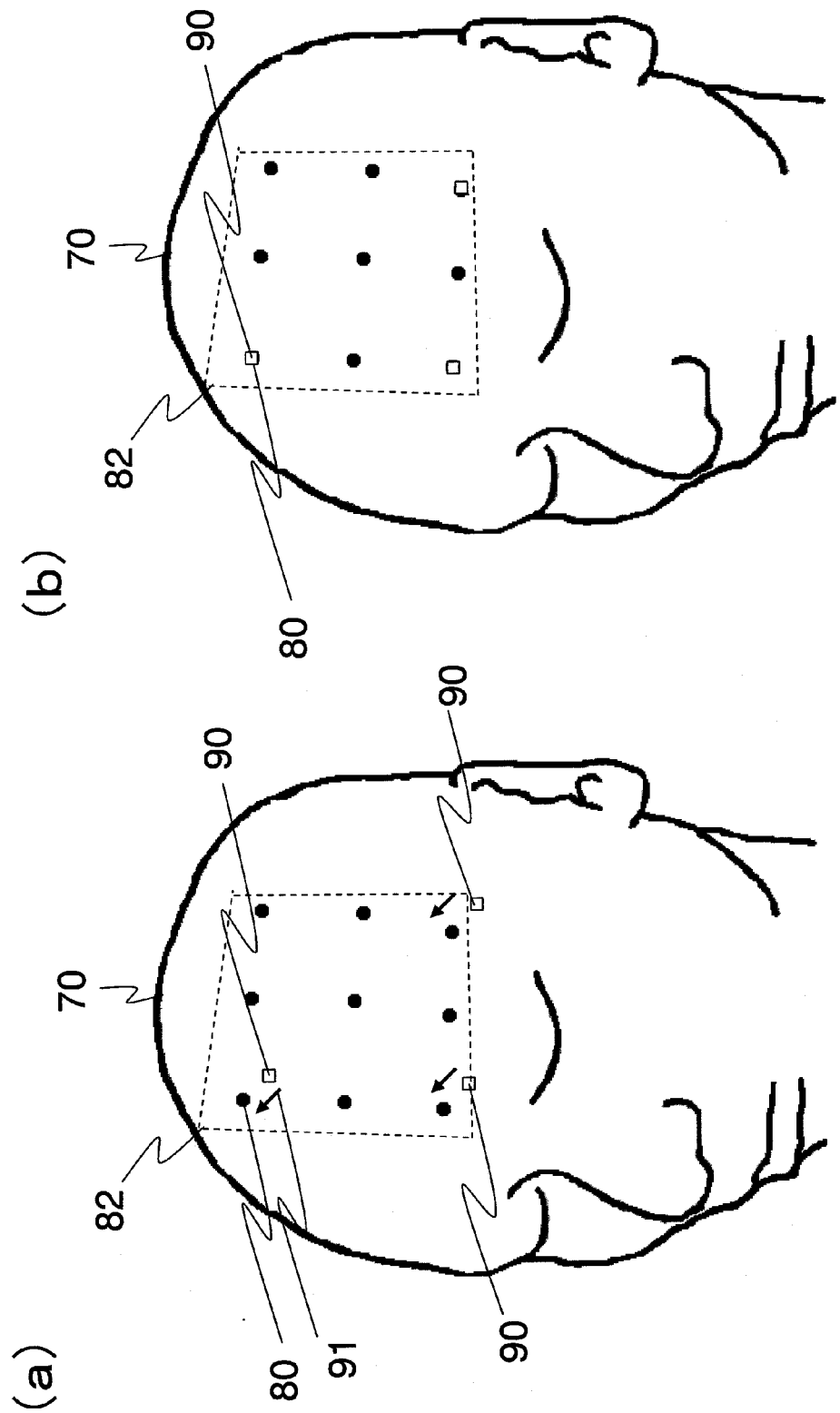
FIG. 7 is a view showing a second embodiment of the present invention.

Here, the second embodiment will be described mainly using FIG. 7. The difference from the first embodiment is that the spatial positions of the optical fiber setting points 80 which have been measured in the past and the stored spatial position of a plurality of registered points 90 can be easily compared.

FIG. 7(a) is a view showing the application position of the probe holder 23 before adjustment, and FIG. 7(b) shows the application position of the probe holder 23 after the adjustment.

In FIG. 7(a), the optical fiber setting points 80 which have been measured in the past are displayed on the head-surface image 70 by the method described in the first embodiment. The mobile magnetic sensor 53 is applied to at least three places of the optical fiber setting positions (holes) of the probe holder 23, and the spatial positions of the mobile magnetic sensor 53 at the three places are respectively stored in the storage unit 38. The storage unit 38 stores, for example the spatial positions of the three places equivalent to the optical fiber setting positions (holes) at the corners of the probe holder 23. The stored spatial positions at the three places are displayed on the display unit 36 as the registered points 90.

Then the reference image creating unit 42 compares the spatial position of the optical setting points 80 which have been measured in the past and stored in the storage unit 38 and the spatial position of the stored registered points 90. The targets for comparison are the spatial position of the register points 90 (three places) and the spatial position of the optical setting points 80 (three places) corresponding to the position of the registered points 90. In the case that there is displacement in the spatial positions of the optical fiber setting points 80 and the registered points 90, the reference image crating unit 42 creates marks (arrows 91) which indicate the distance and the direction equivalent to the displacement and causes the display unit 36 to display them.

The examiner adjusts the application position of the probe holder 23 referring to the displayed marks (arrows 91). After adjusting the application position of the probe holder 23, the optical fiber setting points 80 and the registered points 90 match as shown in FIG. 7(b). At this time, the marks (arrows 91) for indicating the distance and the direction equivalent to the displacement are not displayed on the display unit 36.

As described above, in accordance with the second embodiment, the examiner can verify whether the application position of the probe holder 23 which has been measured in the past and the currently measured application position of the probe holder 23 match by confirming the registered marks 90 or marks (arrows 91).

Embodiment 3

Here, the third embodiment will be described using FIGS. 8 and 9. The difference from the first and second embodiments is that the brain-surface points corresponding to the head-surface points displayed on the head-surface image are displayed on the brain-surface image.

Figure 8:
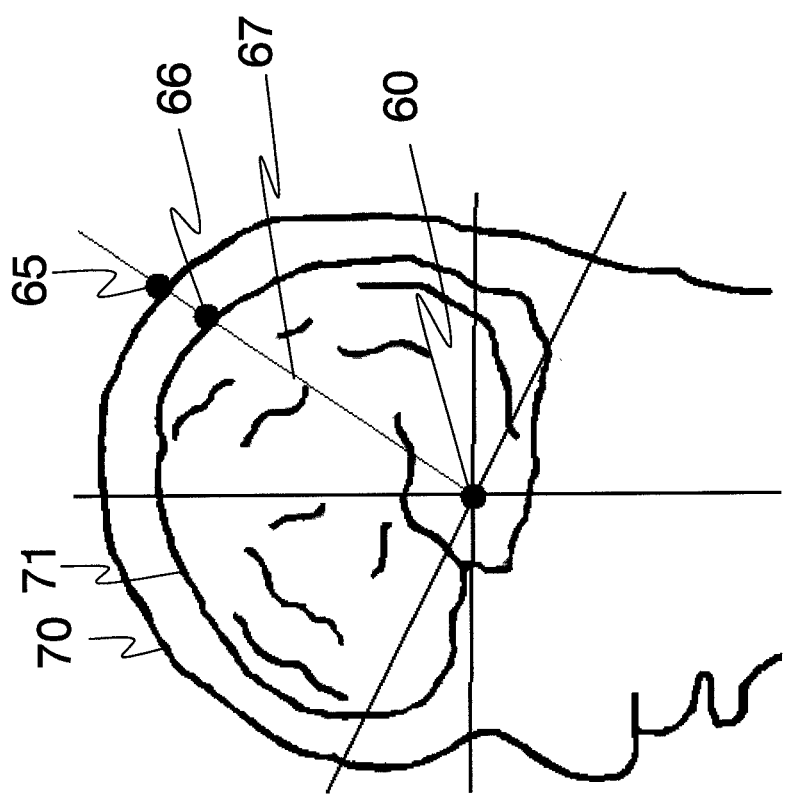
FIG. 8 is a view showing a third embodiment of the present invention.

As shown in FIG. 8, the brain-surface point creating unit 46 creates on a brain-surface image 71 the spatial position of the brain surface of the object 22 corresponding to the head-surface point 65 of the mobile magnetic sensor 53 as a brain-surface point 66.

In concrete terms, the brain-surface image 71 which is the 3-dimensional image of the object 22 obtained using a 3-dimensional image diagnostic apparatus such as an MRI apparatus or an X-ray CT apparatus is stored in the storage unit 38 in advance, and the brain-surface point creating unit 46 loads the brain-surface image 71 of the object 22 from the storage unit 38. Then the display unit 36 displays the brain-surface image 71 of the object 22.

At the time of displaying the head-surface image 70 and the brain-surface image 71, the display unit 36, using the spatial position, etc. of the reference point 60 calculated by the stored three points (nasion (nasal root) 63, right ear upper-end portion 61 and left ear upper-end portion 62), matches and displays the respective positions of the head-surface image 70 and the brain-surface image 71. Then the display unit 36 makes the head-surface image 70 translucent on the display so that the brain-surface image 71 can be confirmed.

The examiner applies the penpoint of the mobile magnetic sensor 53 on the head surface of the object 22. The head-surface point creating unit 45 creates on the head-surface image 70 the spatial position of the head surface of object 22 corresponding to the spatial position of the mobile magnetic sensor 53 as the head-surface point 65.

The brain-surface point creating unit 46 calculates a straight line 67 which passes through the reference point (original point) 60 and the head-surface point 65 as shown in FIG. 8 from the spatial positions of the reference point (original point) 60 and the head-surface point 65 calculated as the spatial point of the mobile magnetic sensor 53.

Then the brain-surface point creating unit 46 calculates the point at which the calculated straight line 67 intersects with the brain-surface image 71 as the brain-surface point 66. Since the brain surface is anatomically located at about 2 cm depth from the head surface, the brain-surface point creating unit 46 sets the distance between the head surface and the brain surface as, for example 2 cm and calculates the point on the straight line 67 which is at 2 cm from the head-surface point 65 toward the reference point 60 as the brain-surface point 66. The display unit 36 displays the brain-surface point 66 on the brain-surface image 71 based on the spatial position of the calculated brain-surface point 66. The brain-surface point creating unit 46, by arbitrarily setting the distance between the head surface and the brain surface using the input/output unit 40, may also calculate the point on the straight line 67 which is at an arbitrary distance from the head-surface point 65 toward the reference point 60 as the brain-surface point 66.

Further, display unit 36 can calculate the spatial position of the brain-surface point 66 in accordance with the movement (change of the spatial position) of the mobile magnetic sensor 53 and displays on the brain-surface image 71 the brain-surface point 66 corresponding to the movement of the mobile magnetic sensor 53 in real time.

Figure 9:
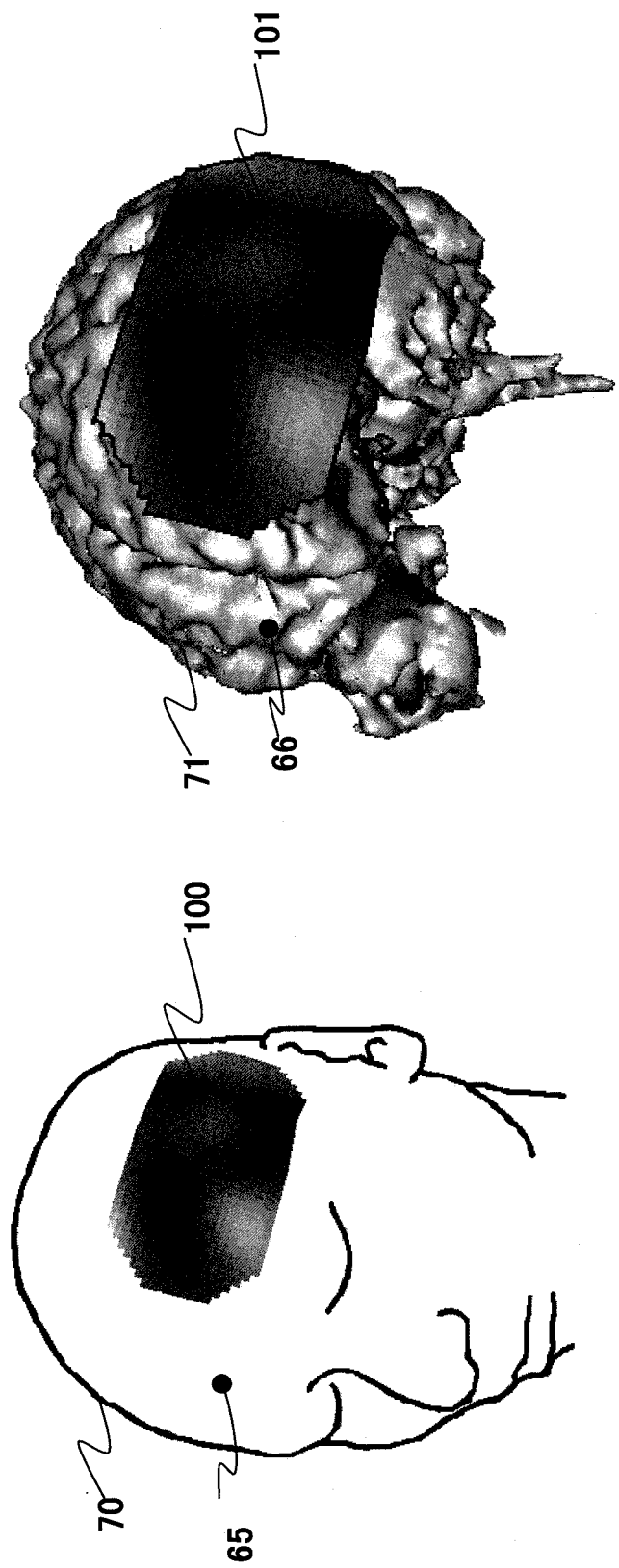
FIG. 9 is a view showing the third embodiment of the present invention.

While the head-surface image 70 with the head-surface point 65 and the brain-surface 71 with the brain-surface point 66 are superimposed and displayed in FIG. 8, the display unit may also display the head-surface image 70 with the head-surface point 65 and the brain-surface 71 with the brain-surface point 66 separately on the same screen as shown in FIG. 9.

The image creating unit 37 creates a 3-dimensional image based on the concentration change of oxygenated hemoglobin, concentration change of deoxygenated hemoglobin and concentration change of total hemoglobin, and matches the spatial position of the created 3-dimensional image and the spatial position of the head-surface image 70 and the brain-surface image 71 using the spatial position of the reference point 60. The display unit 36 causes a 3-dimensional grayscale image 100 to be displayed on the head-surface image 70, and causes a 3-dimensional grayscale image 101 to be displayed on the brain-surface image 71. By translucently superimposing the 3-dimensional grayscale image 100 over the brain-surface image 71 based on the concentration change of hemoglobin, the examiner can specifically recognize which region of the brain is being active.

Also, the display unit 36 can display the head-surface point 65 on the head-surface image 70 and display the brain-surface point 66 on the brain-surface image 71 using the methods in the first embodiment and the second embodiment.

As described above, in accordance with the third embodiment, the examiner can verify the head-surface point 65 and the brain-surface point 66 displayed by applying the penpoint of the mobile magnetic sensor 53 on the head surface of the object 22, whereby making it possible to verify in real time the setting points of the optical fibers 20 and 26 of the probe holder 23 that affixes the respective optical fibers 20 and 26.

DESCRIPTION OF REFERENCE NUMERALS

10: light source unit
12: light measurement unit
14: control unit
16: semiconductor laser
18: optical module
20: irradiating optical fiber (irradiating light transmission unit)
22: object
23: probe holder
26: detecting optical fiber (detecting light transmission unit)
28: photoelectric transducer
30: lock-in amplifier
32: A/D converter
34: signal processing unit
36: display unit
38: storage unit
40: input/output unit
42: reference image creating unit
50: magnetic unit (position sensor unit)

The invention claimed is:

1. A biological optical measurement instrument comprising:
a plurality of light transmission units;
a light source unit configured to irradiate near-infrared light to an object to be examined;
a light measurement unit configured to measure an intensity of transmitted light at a plurality of measurement points in the object;
a probe holder configured to affix the plurality of light transmission units;
a signal processing unit configured to process and image measurement data from the light measurement unit;
a display unit configured to display a processing result from the signal processing unit;
a mobile magnetic position sensor which is movable in a 3-dimensional space and configured to detect a spatial position in a 3-dimensional space;
a head-surface image creating unit configured to create a head-surface image of the object;
a head-surface point creating unit configured to create on the head-surface image a head-surface point corresponding to the spatial position detected by the mobile magnetic position sensor;

a storage unit configured to store a brain-surface image of the object obtained using a 3-dimensional image diagnostic apparatus;

a brain-surface image creating unit configured to read out the brain-surface image from the storage unit and create the brain-surface image; and a brain-surface point creating unit configured to:
create on the brain-surface image a brain-surface point corresponding to the head-surface point specified by the mobile magnetic position sensor,
calculate a straight line which passes through a reference point inside a head and the head-surface point from the spatial position of the reference point in a head region acquired from a head surface of the object and the spatial position of the head-surface point, and
calculate a point at which the calculated straight line intersects with the brain-surface image as the brain-surface point.

2. The biological optical measurement instrument according to claim 1, further comprising a light transmission unit setting point creating unit configured to create, on the head-surface image, a plurality of light transmission unit setting points which have been measured in a past on a basis of spatial positions of the plurality of light transmission unit setting points of the probe holder which have been measured in the past.

3. The biological optical measurement instrument according to claim 2, wherein the storage unit is further configured to store the spatial positions of the light transmission unit setting positions of the probe holder which have been measured in the past.

4. The biological optical measurement instrument according to claim 3, which applies the mobile magnetic position sensor to at least three places of the light transmission unit setting positions of the probe holder and stores the spatial positions of the mobile magnetic position respectively in the storage unit, wherein the display unit displays on the head-surface image at least three places of stored spatial positions as registered points.

5. The biological optical measurement instrument according to claim 4, comprising:
a reference image creating unit further configured, in a case that there is displacement between positions of the light transmission unit setting point and a registered point, to create marks, on the head-surface image, that indicate a distance and direction equivalent to the displacement.

6. The biological optical measurement instrument according to claim 2, further comprising:
a measurement point creating unit configured to create on the head-surface image a measurement point corresponding to a measurement position equivalent to a midpoint of the plurality of light transmission unit setting points.

7. The biological optical measurement instrument according to claim 2,
wherein the storage unit is further configured to stores the head-surface image, and
wherein the head-surface image creating unit is further configured to create a head-surface image corresponding to a size or shape of the head region of the object on a basis of the spatial position in the head surface of the object.

8. The biological optical measurement instrument according to claim 2, further comprising:
a reference image creating unit configured to create on the head-surface image a holder frame equivalent to the circumference of the probe holder from the spatial positions of the plurality of light transmission unit setting points which have been measured in the past.

9. The biological optical measurement instrument according to claim 1, wherein the 3-dimensional space is given by a magnetic source configured to generate a magnetic field of 3-axis orthogonal system, in which a reference position in a relevant 3-dimensional space is set by a reference magnetic sensor.

10. The biological optical measurement instrument according to claim 1, wherein the head-surface point creating unit is further configured to creates on the head-surface image a displacement trajectory of the head-surface point corresponding to the spatial position of the mobile magnetic position sensor.

11. The biological optical measurement instrument according to claim 1,
wherein the signal processing unit is further configured to create a 3-dimensional image in which a hemoglobin variation signal is interpolated for each channel on a basis of the measurement data from the light measurement unit, and
wherein the display unit is further configured to displays on the head-surface image the 3-dimensional image with the head-surface point.

* * * * *